(12) United States Patent
Li

(10) Patent No.: US 6,343,110 B1
(45) Date of Patent: Jan. 29, 2002

(54) METHODS AND APPARATUS FOR SUBMILLIMETER CT SLICES WITH INCREASED COVERAGE

(75) Inventor: Jianying Li, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/625,295

(22) Filed: Jul. 25, 2000

(51) Int. Cl.$^7$ .............................................. G01N 23/00
(52) U.S. Cl. .............................. 378/19; 378/207; 378/4
(58) Field of Search ............................. 378/19, 207, 4

(56) References Cited

U.S. PATENT DOCUMENTS

| | | | |
|---|---|---|---|
| 4,982,417 A | * | 1/1991 | Kopinek et al. ............... 378/70 |
| 5,625,663 A | * | 4/1997 | Swerdloff et al. ............ 378/65 |
| 5,864,598 A | | 1/1999 | Hsieh et al. |
| 6,243,438 B1 | * | 6/2001 | Nahaliel et al. ............... 378/19 |

OTHER PUBLICATIONS

Application of Hsieh et al., "Methods and Apparatus for Generating Thin–slice Imaging Data on a Multi–Slice Imaging System," filed May 8, 2000, Ser. No. 09/566,018.

* cited by examiner

Primary Examiner—David V. Bruce
Assistant Examiner—Irakli Kiknadze
(74) Attorney, Agent, or Firm—Armstrong Teasdale LLP; Christian G. Cabou

(57) ABSTRACT

One embodiment of the present invention is a method for imaging an object using a multi-slice computed tomography (CT) imaging system having a radiation source and a detector, the detector having a plurality of detector rows configured to acquire projection data from a scanned object between the radiation source and the detector, wherein each of the detector rows is perpendicular to and has a thickness in a z-direction. The method includes steps of collimating a radiation beam from the radiation source into a plurality of separate beam portions transverse to the z-direction so that the separate beam portions pass through the object and impinge on the detector rows; scanning the object using the plurality of separate beam portions to acquire projection data; and reconstructing an image of the object utilizing the acquired projection data.

36 Claims, 3 Drawing Sheets

METHODS AND APPARATUS FOR SUBMILLIMETER CT SLICES WITH INCREASED COVERAGE

BACKGROUND OF THE INVENTION

This invention relates generally to computed tomography (CT) imaging and more particularly to methods and apparatus for generating CT imaging data using a multi-slice imaging system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

In known CT systems the x-ray beam is projected from the x-ray source through a pre-patient collimator that defines the x-ray beam profile in the patient axis, or z-axis. The collimator typically includes x-ray-absorbing material with an aperture therein for restricting the x-ray beam.

By imposing limitations on such factors as collimator aperture size and slice thickness, CT imaging systems provide image resolution. A collimator defines the dimensions of the x-ray beam(s), particularly its width. A collimator's aperture width typically controls the slice thickness as measured along the z-axis. Known apertures are typically linear or rectangular. By defining x-ray beam width, a collimator determines the thickness of an individual slice or group of slices. By reducing the slice thickness, the image resolution is improved. For example, by passing an x-ray beam through a collimator with a 1 millimeter aperture, the beam output from the collimator will have a 1 millimeter thickness.

Known CT systems typically utilize collimators having at least one 1 mm aperture. While 1 millimeter or higher slices are effective for many CT system applications, in some CT system applications, a thinner slice thickness is desired. Particularly, in some applications, it is desirable to generate an image with, for example, submillimeter slice images. Such smaller slice images are specifically desirable when patient anatomy differs in areas less than 1 millimeter apart.

One way to obtain thinner slices is to make the detector cells thinner. However, this requires a great amount of hardware redesign and also requires sacrificing scanner coverage and speed in most applications. A minimum slice thickness for at least one CT system is 1.25 millimeters, as determined primarily by detector element pitch size. In order to improve image resolution, it is desirable to reduce slice thickness to less than 1 millimeter. In some applications, a slice thickness as thin as 0.5 millimeter is desired.

It is known to reduce slice thickness of a single-slice imaging system by irradiating a portion of a detector element and deconvolving imaging data to reduce the full-width-at-half-maximum (FWHM) interval of a reconstructed slice profile. It is desirable to achieve similar slice-width reductions on multi-slice systems without reducing coverage. However, difficulties arise in implementing this approach for a multi-slice imaging system because multi-slice sampling is limited by joints between adjacent detector rows.

It would be desirable to improve image resolution in a multi-slice CT system by providing a slice thickness less than 0.5 mm, or submillimeter slices, by using single-slice imaging data collection with multiple x-ray source collimators, different sampling schemes and deconvolution techniques.

BRIEF SUMMARY OF THE INVENTION

There is therefore provided, in one embodiment of the present invention, a method for imaging an object using a multi-slice computed tomography (CT) imaging system having a radiation source and a detector, the detector having a plurality of detector rows configured to acquire projection data from a scanned object between the radiation source and the detector, wherein each of the detector rows is perpendicular to and has a thickness in a z-direction. The method includes steps of collimating a radiation beam from the radiation source into a plurality of separate beam portions transverse to the z-direction so that the separate beam portions pass through the object and impinge on the detector rows; scanning the object using the plurality of separate beam portions to acquire projection data; and reconstructing an image of the object utilizing the acquired projection data.

The above described embodiment provides clinically useful submillimeter scan modes with greatly increased coverage, compared to known methods.

DETAILED DESCRIPTION OF THE INVENTION

Figure 1:
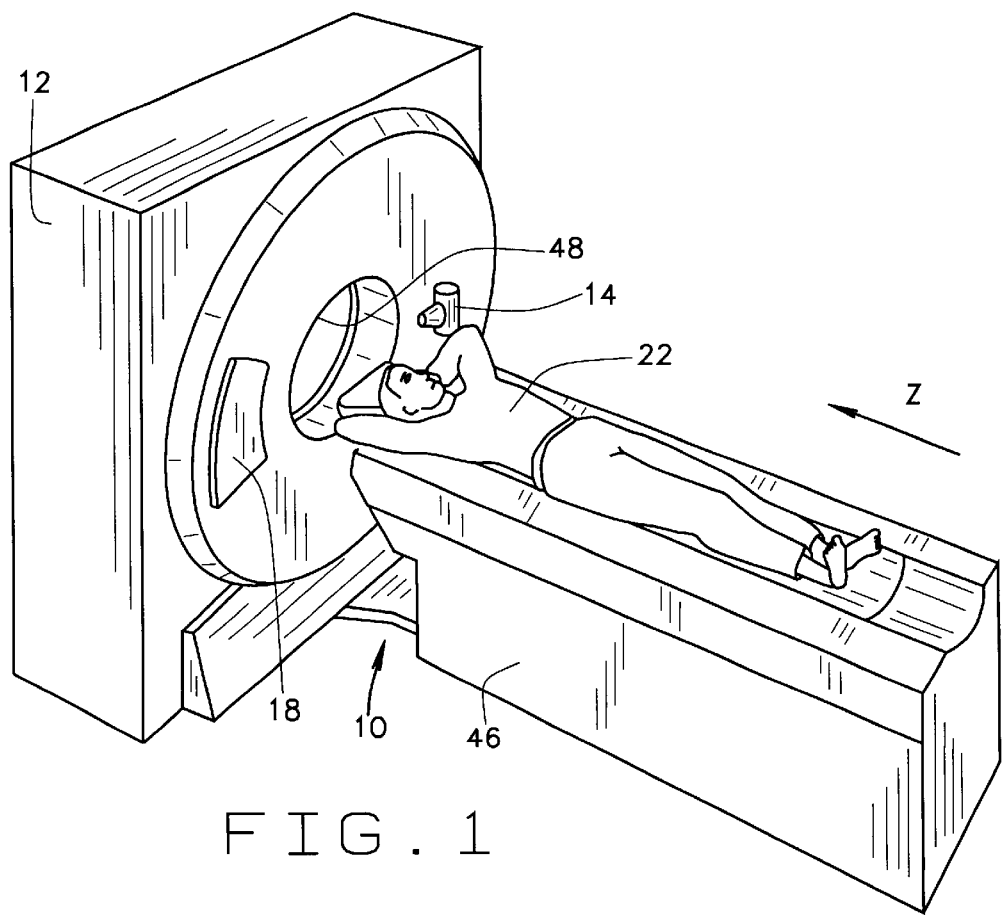
FIG. 1 is a pictorial view of a CT imaging system.
Figure 2:
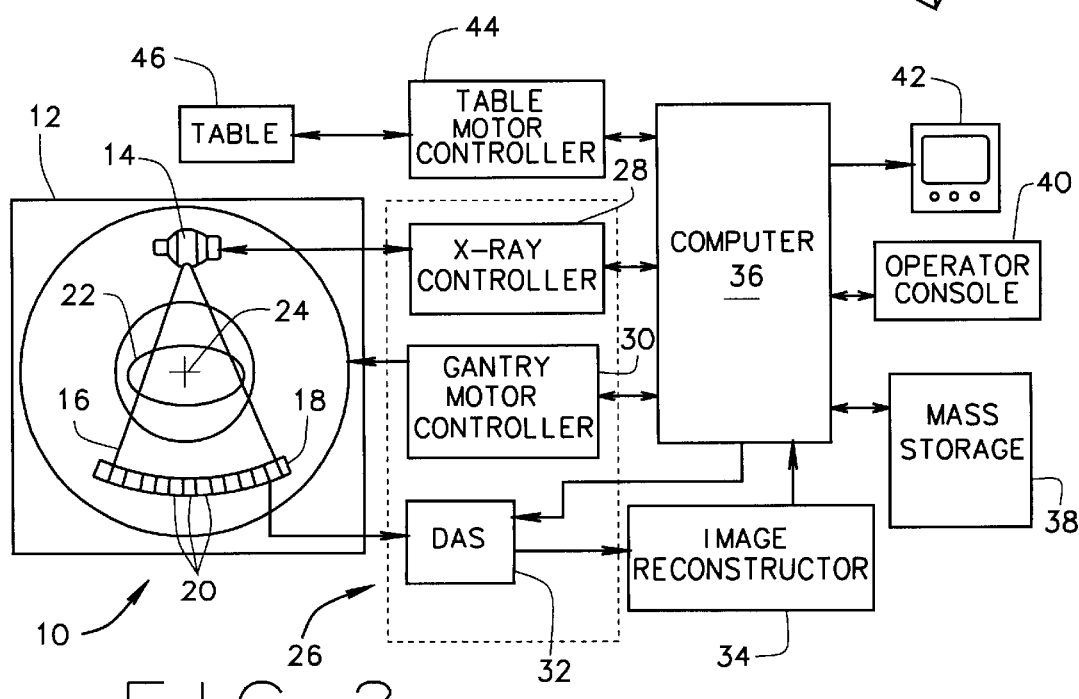
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22 for example a medical patient. Detector array 18 may be fabricated in a single slice or a multi-slice configuration, the latter having a plurality of parallel rows of detector elements. Each detector element 20 produces an electrical signal that represents the intensity of an impinging x-ray beam. As the x-ray beam passes through a patient 22, the beam is attenuated. During a scan to acquire x-ray projection data, gantry 12 and the components mounted thereon rotate about a center of rotation 24. The parallel rows of a multi-slice detector 18 are each perpendicular to the z-axis and are configured to detect x-rays passing through different "slices" of object 22.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. For multi-slice detectors 18, data from parallel rows of detector elements 20 is collected. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In FIG. 2, the z-axis of CT imaging system 10 is not shown because it points directly into the plane of the figure at center of rotation 24.

Figure 3:
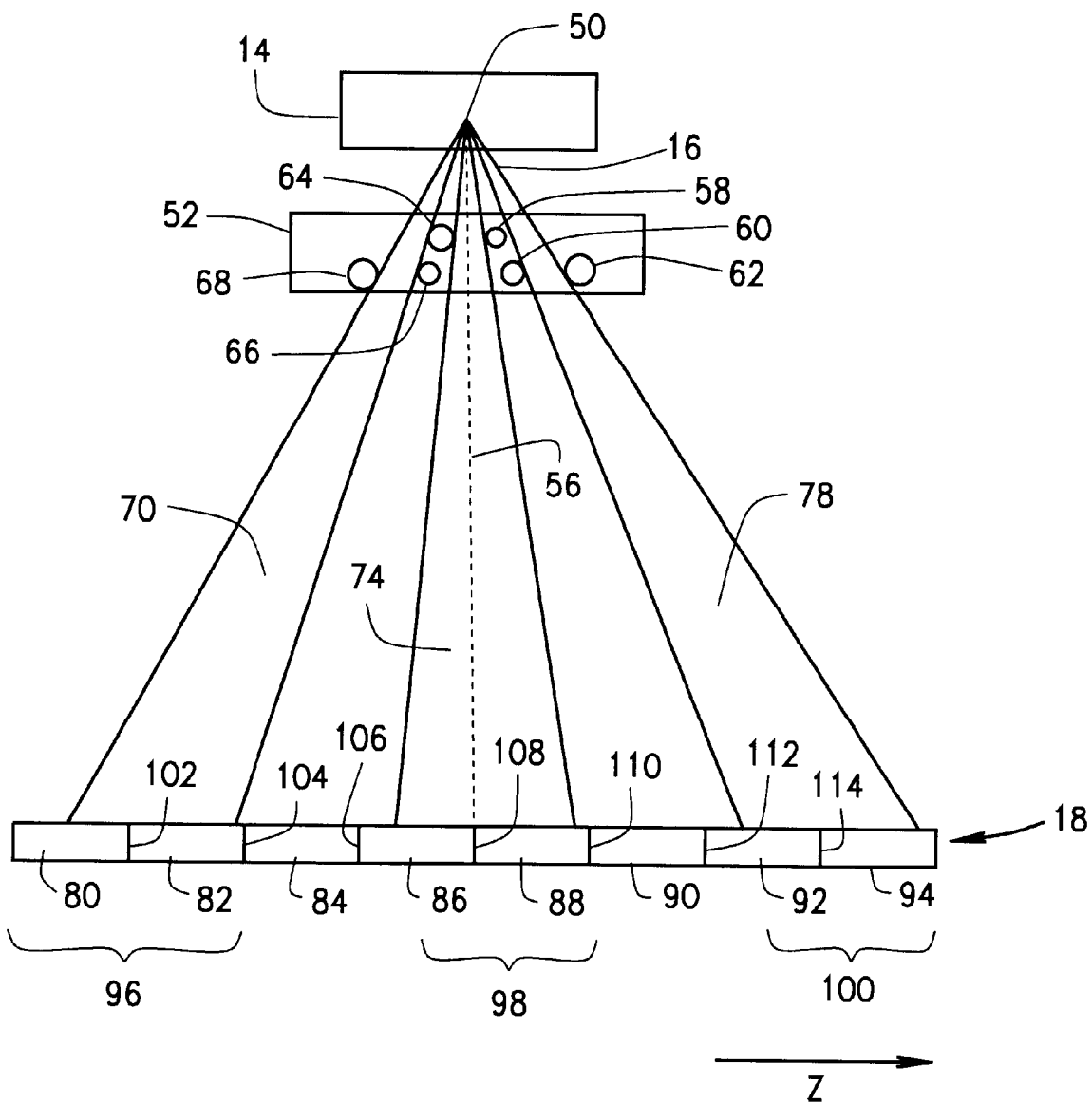
FIG. 3 is a diagram illustrating collimated portions of an x-ray beam of one embodiment of the invention impinging on a multi-slice detector array.

In one embodiment of the present invention using a mutli-slice imaging system 10 and referring to FIG. 3, x-ray beam 16 emanates from a focal spot 50 of source 14. X-ray beam 16 is collimated by a pre-patient collimator array 52 and projected toward detector array 18 along a fan beam axis 56 centered within fan beam 16. Pre-patient collimator array 52 includes a plurality of collimators 58, 60, 62, 64, 66, 68. Pre-patient collimator array 52 collimates fan beam 16 into separate collimated beam portions 70, 74, 78 transverse to the z-direction that pass through object 22 and impinge on rows 80, 82, 84, 86, 88, 90, 92, 94 of detector array 18. In one embodiment, these rows are 1.25 mm thick, and sub-millimeter slices are obtained by operation of collimator array 52 to adjust the thicknesses and locations of beams 70, 74, and 78 relative to detector rows 80, 82, 84, 86, 88, 90, 92, 94. In one embodiment of the present invention, collimator array 52 is configured to selectively operate collimators 58, 60, 62, 64, 66, 68 either independently or in unison. In case a normal slice thickness (e.g., 1.25 mm or more) is needed, for example, collimator array 52 operates collimators 58, 60, 62, 64, 66, 68 in unison to provide a single beam 16 that passes through object 22.

Imaging system 10 slice thickness is reduced in one embodiment by obtaining projection data from pairs 96, 98, 100 of adjacent detector rows that are only partially impinged by collimated beams 70, 74, 78. In this embodiment, beams 70, 74, and 78 are collimated to a thickness less than two detector rows are directed so that each straddles a cell joint 102, 108, 114 between adjacent rows of detector elements. Thus, x-rays only partially impinge the thickness of the impinged detector rows, effectively reducing their thickness for image reconstruction purposes. For example, projection data from at least six partially impinged rows 80, 82, 86, 88, 92, 94 of detector array 18 is acquired during a scan. In this configuration, a pair 96 of outermost detector rows 80, 82 are used to reduce interactions between a center part (i.e., a part impinging rows 86 and 88) and an outer part (i.e., a part impinging rows 80 and 82 on one side, and rows 92 and 94 on another side) of x-ray beam 16. Detector rows 84 and 90 are impinged by a penumbra of x-ray beam 16 (more particularly, a penumbra of a part impinging row 98). Thus, rows 84 and 90 will also produce images, albeit with reduced image quality. These reduced quality images are used in one embodiment to provide additional useful information. (In embodiments having more than 8 detector rows, at least one detector row is between selected detector rows to minimize penumbra interaction.) Either an axial scan or a helical scan is performed to acquire projection data.

Directing collimated beam 78 onto outer rows 92 and 94 and obtaining projection data as described above effectively reduces slice thickness, which is advantageous for some clinical applications. For example, where a full-width-at-half-maximum (FWHM) interval of system 10 is 1.7 millimeters at the iso-center, slice thickness in one embodiment is reduced to a FWHM of 0.85 millimeters. More particularly, a pre-patient collimated portion 78 of radiation beam 16 having a thickness less than two detector rows impinges outer rows 92, 94 of detector array 18 and straddles cell joints 114 between detector elements 20 of these rows. For maximum resolution, each beam portion 70, 74, 78 has a thickness less than two detector rows and each portion straddles the cell joints between only the two adjacent parallel detector rows.

Row groups 96, 98 and 100 are equivalent with respect to achieving sub-millimeter slices. Therefore, the statements above concerning collimated beam 78 applying to row group 100 (i.e., rows 92 and 94) also applies to collimated beam 74 and 70, and to row groups 98 and 96, respectively. However, images from detector rows 84 and 90 have reduced image quality because the penumbra of collimated x-ray beam 16 has less intensity and is less uniform.

In another embodiment, 0.6 millimeter slice images are provided with a plurality of collimators 58, 60, 62, 64, 66, 68 using overlapping scans. Object 22 is scanned using beam portions 70, 74, 78 to acquire projection data from which an image of the object is reconstructed.

In one embodiment, partially overlapping projection data from adjacent detector rows 92, 94 is acquired. Deconvolution is applied separately to each of the rows. For example, a one-sided three-point deconvolution kernel is applied using relationships written as:

$$P'_1(i) = \sum_{k=0}^{N} w_k P_1(i-k) \quad (1)$$

$$P'_2(i) = \sum_{k=0}^{N} w_k P_2(i+k) \quad (2)$$

where:
  $P_1$ and $P_2$ are original projection data samples for two adjacent detector rows 1 and 2;
  $P'_1$ and $P'_2$ are deconvolved image data samples for two adjacent detector rows 1 and 2;
  $w_k$ are deconvolution kernel points;
  k is an index;
  i is an image location index; and
  N is a number of images used to perform the deconvolution plus one (because the index starts from 0). Thus, for a 3-point deconvolution kernel, N is equal to 2.

Deconvolution results are improved when all data samples used in a deconvolution are from the same row, as described in equations (1) and (2).

When one-sided deconvolution is used as described above, centroids of deconvolved image data are shifted compared to the original projection data. Thereafter, the deconvolved and shifted imaging data from rows 92 and 94 is combined to obtain a submillimeter slice thickness.

Figure 4:
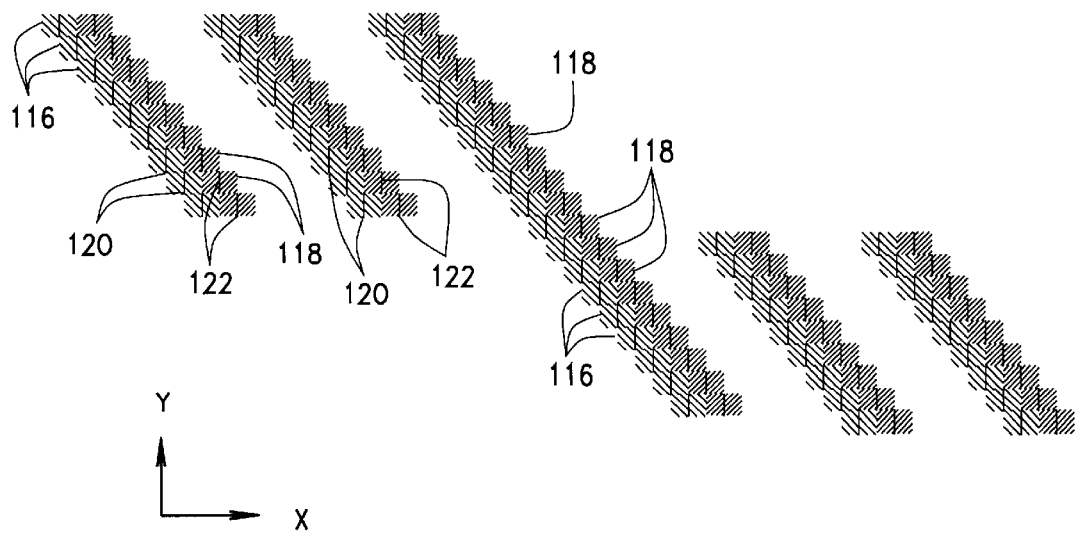
FIG. 4 is an illustration of a sampling scheme with overlap scans to enable deconvolution operation to produce 0.6 mm FWHM slices.

In one embodiment, a sampling pattern represented in FIG. 4 is used to obtain submillimeter slices with limited coverage. In FIG. 4, the x-axis represents a detector location for each of the sampling positions in a z-direction (i.e., the patient direction). The y-axis represents the different sampling positions. For example, at line 1, detectors are at a starting position. At line 2, detector cells have moved a distance in the z-direction to sampling position 2. In the embodiment represented by FIG. 4, after nine scans, the detector cells of detector 18 (or equivalently, table 46) has jumped 8 millimeters to a new position. In FIG. 4, left detector cells 116 are differentiated from right detector cells 118 for purposes of the deconvolution algorithm. Sampling from the same set of cells 116 or 118 is used to perform a convolution to obtain a desired slice thickness. Lines 120, 122 show the sampling center of the detector cell. (FIG. 4 represents a case of overlapping sampling.) In general, detector 18 (or equivalently, table 46) increments at half of a detector sampling width, which in this embodiment, is about 0.84 mm.

More particularly, in the embodiment represented by FIG. 4, overlapping scans are performed, with table 46 stepping less than a row thickness between scans. For example, table 46 steps 0.42 mm between scans to produce 0.84 mm FWHM slices. The overlapping scans are deconvolved using the deconvolution algorithm, as described above. In one embodiment, after deconvolution, image data from adjacent pairs of rows of detector array 18 are combined to reduce noise while maintaining the same thin slice profile. For example, image data from rows 80 and 82, 86 and 88, and 92 and 94 are combined to produce data representative of three separate slices. In one embodiment, after nine scans, motorized table 46 is incremented 8 millimeters followed by a normal 0.42 millimeter increment to increase coverage and avoid unnecessary over-sampling.

Figure 5:
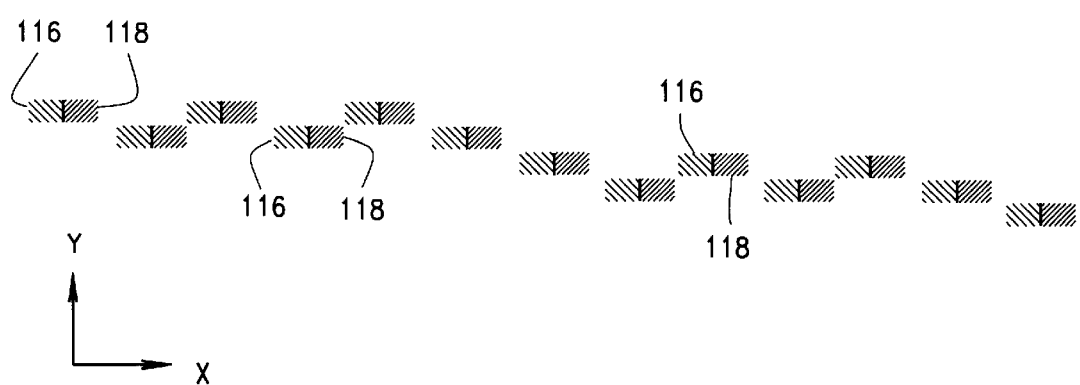
FIG. 5 is an illustration of a sampling scheme without overlap scans to produce 0.8 FWHM slices with greater coverage.

In another embodiment, where both large coverage and sub-millimeter slices are required, an uneven z-direction sampling represented in FIG. 5 is used. Non-overlapping scans are performed and the z-axis increment of motorized table 46 is varied in an alternating pattern. After the first scan, table 46 is incremented 2 millimeters. In the next scan, table 46 is incremented 9.5 millimeters. A 2 millimeter increment follows for the next scan. This embodiment enables a known 8-slice scanner to cover 210 mm in 30 seconds with a 0.8 sec rotation speed, yielding a slice thickness of 0.8 millimeter FWHM.

It will thus be recognized by those skilled in the art that embodiments of the present invention provide submillimeter scan modes with greatly increased coverage, as compared to known CT scanning methods and apparatus. Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

While the invention has been described in terms of various specific embodiments, those skilled in the art will recognize that the invention can be practiced with modification within the spirit and scope of the claims.

What is claimed is:

1. A method for imaging an object using a multi-slice computed tomography (CT) imaging system having a radiation source and a detector, the detector having a plurality of detector rows configured to acquire projection data from a scanned object between the radiation source and the detector, each of the detector rows being perpendicular to and having a thickness in a z-direction;

said method comprising the steps of:
  collimating a radiation beam from the radiation source into a plurality of separate beam portions transverse to the z-direction so that the plurality of separate beam portions pass through the object and impinge on the detector rows;
  scanning the object using the plurality of separate beam portions to acquire projection data; and
  reconstructing an image of the object utilizing the acquired projection data.

2. A method in accordance with claim 1 wherein collimating the radiation beam comprises using a collimation array having a plurality of collimators to collimate the radiation beam.

3. A method in accordance with claim 1 wherein collimating the radiation beam comprises independently operating a plurality of collimators.

4. A method in accordance with claim 1 wherein collimating the radiation beam comprises operating a plurality of collimators in unison.

5. A method in accordance with claim 1 wherein collimating the radiation beam comprises the step of collimating the radiation beam to impinge on outer rows of the detector.

6. A method in accordance with claim 5 wherein collimating the radiation beam to impinge on the outer rows of detectors comprises generating a first collimated beam portion having a thickness less than two detector rows.

7. A method in accordance with claim 6 wherein the first collimated beam portion straddles cell joints between an adjacent pair of detector rows.

8. A method in accordance with claim 7 wherein the first collimated beam portion straddles cell joints between only two adjacent rows of detectors.

9. A method in accordance with claim 1 wherein scanning the object comprises the step of performing an axial scan.

10. A method in accordance with claim 1 wherein scanning the object comprises the step of performing a helical scan.

11. A method in accordance with claim 1 wherein scanning an object comprises the step of acquiring projection data from at least six partially impinged rows of the detector.

12. A method in accordance with claim 1 wherein scanning an object comprises the step of acquiring projection data from a plurality of adjacent pairs of partially impinged detector cell rows.

13. A method in accordance with claim 1 wherein scanning an object comprises the step of acquiring projection data by performing uneven sampling in the z-direction.

14. A method in accordance with claim 1 wherein scanning the object comprises the step of performing overlapping scans of the object.

15. A method in accordance with claim 14 wherein the CT imaging system comprises a moveable table configured to support the object between the radiation source and the detector, and wherein performing overlapping scans of the object comprising the step of stepping the table a distance less than a row thickness between the overlapping scans.

16. A method in accordance with claim 1 wherein reconstructing an image comprises the step of deconvolving a plurality of partially overlapping projection data from adjacent detector rows to produce a plurality of image slices.

17. A method in accordance with claim 16 wherein generating a plurality of image slices comprises the step of separately deconvolving the partially overlapping projection data for each pair of adjacent detector rows.

18. A method in accordance with claim 1 wherein the CT imaging system further comprises a movable table configured to support an object between the radiation source and the detector, and the detector is a multi-slice detector having a plurality of rows of detector elements; wherein scanning the object to acquire projection data comprises the step of varying a z-axis table increment in an alternating pattern to obtain non-overlapping projection data along the z-axis from the plurality of rows of detector elements.

19. A multi-slice computed tomography (CT) imaging system comprising a radiation source and a detector, the detector having a plurality of detector rows configured to acquire projection data from a scanned object between the radiation source and the detector, each of the detector rows being perpendicular to and having a thickness in a z-direction;
said system being configured to:
collimate a radiation beam from the radiation source into a plurality of separate beam portions transverse to the z-direction so that the plurality of separate beam portions pass through an object to be scanned and impinge on the detector rows;
scan the object using the plurality of separate beam portions to acquire projection data; and
reconstruct an image of the object utilizing the acquired projection data.

20. A system in accordance with claim 19 further comprising a plurality of collimators configured to collimate the radiation beam.

21. A system in accordance with claim 20 wherein the plurality of collimators are configured to operate independently.

22. A system in accordance with claim 19 wherein the plurality of collimators are configured to operate in unison.

23. A system in accordance with claim 19 wherein said system being configured to collimate the radiation beam comprises said system being configured to collimate the radiation beam to impinge on outer rows of the detector.

24. A system in accordance with claim 23 further configured to generating a first collimated beam portion having a thickness less than two detector rows.

25. A system in accordance with claim 24 wherein cells of adjacent detector rows are joined at cell joints, and said system being configured to generate a first collimated beam portion comprises said system being configured to generate a first collimated beam portion straddling cell joints between an adjacent pair of detector rows.

26. A system in accordance with claim 25 wherein said system being configured to generate a first collimated beam portion comprises said system being configured to generate a first collimated beam portion straddling cell joints between only two adjacent rows of detectors.

27. A system in accordance with claim 19 wherein to scan an object, said system is configured to perform an axial scan.

28. A system in accordance with claim 19 wherein to scan an object, said system is configured to perform a helical scan.

29. A system in accordance with claim 19 wherein to scan an object, said system is configured to acquire projection data from at least six partially impinged rows of the detector.

30. A system in accordance with claim 19 wherein to scan an object said system is configured to acquire projection data from a plurality of adjacent pairs of partially impinged detector cell rows.

31. A system in accordance with claim 19 wherein to scan an object, said system is configured to acquire projection data by performing uneven sampling in the z-direction.

32. A system in accordance with claim 19 wherein to scan an object, said system is configured to perform overlapping scans of the object.

33. A system in accordance with claim 32 further comprising a moveable table configured to support an object to be scanned between the radiation source and the detector, and wherein to perform overlapping scans of the object, said system is configured to step the table a distance less than a row thickness between the overlapping scans.

34. A system in accordance with claim 19 wherein to reconstruct an image, said system is configured to deconvolve a plurality of partially overlapping projection data from adjacent detector rows to produce a plurality of image slices.

35. A system in accordance with claim 34 wherein to generate a plurality of image slices, said system is configured to separately deconvolve the partially overlapping projection data for each pair of adjacent detector rows.

36. A system in accordance with claim 19 further comprising a movable table configured to support an object between the radiation source and the detector, and wherein the detector is a multi-slice detector having a plurality of rows of detector elements; and to scan an object to acquire projection data, said system is configured to vary a z-axis table increment in an alternating pattern to obtain non-overlapping projection data along the z-axis from the plurality of rows of detector elements.

* * * * *